US008665101B2

(12) United States Patent
Solomon

(10) Patent No.: US 8,665,101 B2
(45) Date of Patent: Mar. 4, 2014

(54) SYSTEM METHOD AND DEVICE FOR LEAK DETECTION AND LOCALIZATION IN A PIPE NETWORK

(75) Inventor: David Solomon, Zihron Yacov (IL)

(73) Assignee: Aquarius Spectrum Ltd., Netanya (IL)

( * ) Notice: Subject to any disclaimer, the term of this patent is extended or adjusted under 35 U.S.C. 154(b) by 456 days.

(21) Appl. No.: 12/830,920

(22) Filed: Jul. 6, 2010

(65) Prior Publication Data
US 2012/0007743 A1    Jan. 12, 2012

Related U.S. Application Data

(60) Provisional application No. 61/281,199, filed on Nov. 16, 2009, provisional application No. 61/293,721, filed on Jan. 11, 2010.

(51) Int. Cl.
G08B 21/00 (2006.01)

(52) U.S. Cl.
USPC .............. 340/605; 702/51; 702/54; 702/56; 73/40; 73/152.58

(58) Field of Classification Search
USPC ......... 340/605; 702/51, 54, 56; 73/40, 152.58
See application file for complete search history.

(56) References Cited

U.S. PATENT DOCUMENTS

| | | | | |
|---|---|---|---|---|
| 3,673,855 A * | 7/1972 | Garday et al. | | 73/40 |
| 4,940,976 A | 7/1990 | Gastouniotis et al. | | |
| 4,958,296 A * | 9/1990 | Saitoh et al. | | 702/51 |
| 5,272,646 A * | 12/1993 | Farmer | | 702/51 |
| 5,333,501 A * | 8/1994 | Okada et al. | | 73/592 |
| 5,974,862 A * | 11/1999 | Lander et al. | | 73/40.5 A |
| 6,226,598 B1 * | 5/2001 | De Vanssay et al. | | 702/48 |
| 6,246,677 B1 * | 6/2001 | Nap et al. | | 370/346 |
| 6,567,006 B1 * | 5/2003 | Lander et al. | | 340/605 |
| 6,611,769 B2 | 8/2003 | Olson | | |
| 6,725,878 B1 * | 4/2004 | Nawa et al. | | 137/487.5 |
| 6,957,157 B2 * | 10/2005 | Lander | | 702/56 |
| 7,007,545 B1 | 3/2006 | Martinek | | |
| 7,596,458 B2 * | 9/2009 | Lander | | 702/56 |
| 7,668,670 B2 * | 2/2010 | Lander | | 702/51 |
| 7,891,246 B2 * | 2/2011 | Lander | | 73/592 |
| 8,116,071 B2 * | 2/2012 | Showcatally | | 361/664 |
| 2002/0073768 A1 * | 6/2002 | Joynes | | 73/40.5 A |
| 2003/0079774 A1 * | 5/2003 | Reyman | | 137/38 |
| 2003/0084732 A1 * | 5/2003 | Ehrlich et al. | | 73/861.27 |
| 2003/0167847 A1 * | 9/2003 | Brown et al. | | 73/592 |
| 2003/0183018 A1 * | 10/2003 | Addink et al. | | 73/861.69 |
| 2005/0060105 A1 * | 3/2005 | Lander | | 702/51 |
| 2006/0191323 A1 * | 8/2006 | Garabedian et al. | | 73/40 |
| 2007/0062260 A1 * | 3/2007 | Wenger et al. | | 73/54.01 |

(Continued)

FOREIGN PATENT DOCUMENTS

WO     2006/044793 A2    4/2006

Primary Examiner — Benjamin C Lee
Assistant Examiner — Quang D Pham
(74) Attorney, Agent, or Firm — Foley & Lardner LLP

(57) ABSTRACT

The invention provides a system for leak detection of a fluid in a pipe network. The system includes flow meters, and vibration detectors adapted to be attached to a pipe at a location in the pipe network. A processor analyzes signals generated by the flow meters and vibration detectors to identify the presence of one or more leaks in the pipe network. The invention also provides a method for detecting and localizing leaks in a pipeline network, and a device comprising a flow meter integral with a vibration detector for use in the system of the invention.

9 Claims, 8 Drawing Sheets

(56) References Cited

U.S. PATENT DOCUMENTS

| | | | |
|---|---|---|---|
| 2007/0234784 A1* | 10/2007 | Kates | 73/40 |
| 2008/0284174 A1* | 11/2008 | Nagler | 290/54 |
| 2009/0013806 A1* | 1/2009 | Miller et al. | 73/865.8 |
| 2009/0223129 A1* | 9/2009 | De Radigues et al. | 48/194 |
| 2009/0303058 A1* | 12/2009 | Goodman et al. | 340/605 |
| 2010/0156632 A1* | 6/2010 | Hyland et al. | 340/540 |
| 2011/0012738 A1* | 1/2011 | Nakamura et al. | 340/632 |
| 2011/0093220 A1* | 4/2011 | Yang et al. | 702/51 |

* cited by examiner

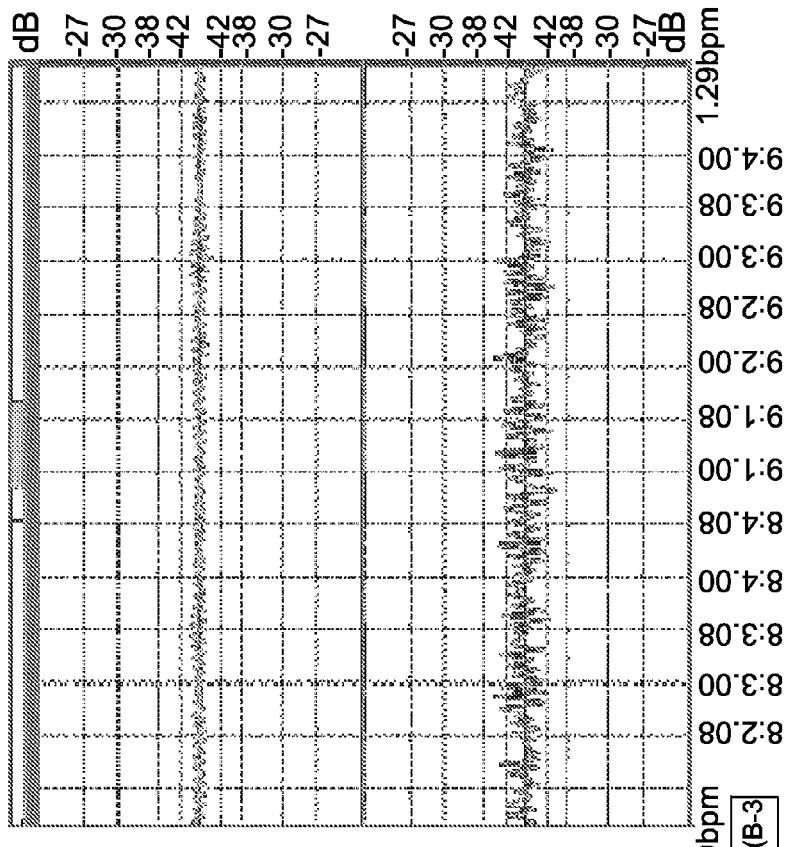

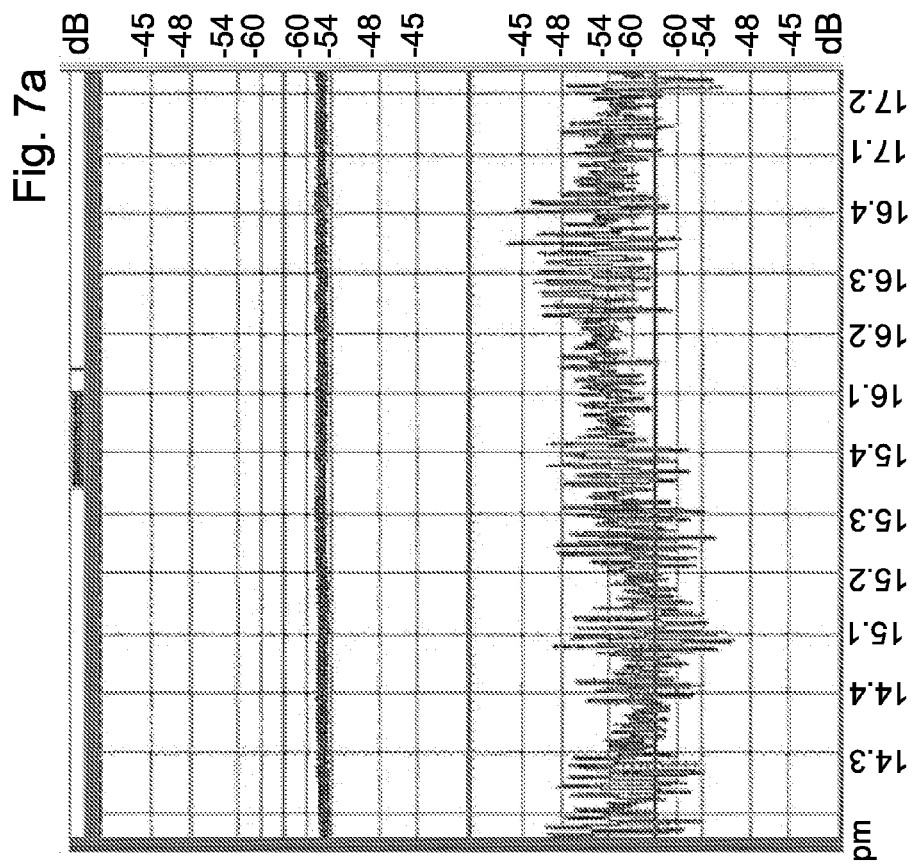
Fig. 7a
Fig. 7b
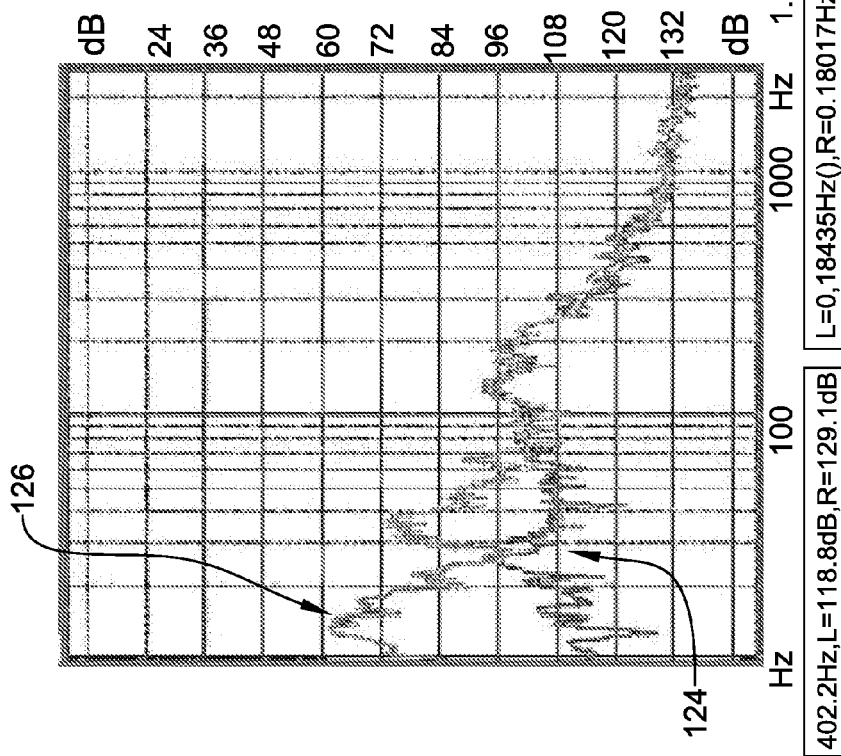
Fig. 7c

SYSTEM METHOD AND DEVICE FOR LEAK DETECTION AND LOCALIZATION IN A PIPE NETWORK

This is a Non-Provisional Application filed under 35 U.S.C. 111(a), filed on Jul. 6, 2010, an application claiming the benefit under 35 USC 119(e) of U.S. Provisional Application No. 61/281,199, filed on Nov. 16, 2009, and an application claiming the benefit under 35 USC 119(e) of U.S. Provisional Application No. 61/293,721, filed on Jan. 11, 2010, the content of each of which is hereby incorporated by reference in its entirety.

FIELD OF THE INVENTION

This invention relates to systems, methods and devices for leak detection.

BACKGROUND OF THE INVENTION

Electronic automatic meter reading (AMR) devices are used for flow metering in a pipeline. These devices typically use an electronic unit attached to a conventional magneto-mechanical or electronic flow meter, for example as disclosed in U.S. Pat. Nos. 4,940,976 and 6,611,769. Magneto-mechanical flow meters typically measure integrative water consumption by means of a mechanical gear. The accumulated liquid consumption is read by opto-electronic circuits, or by piezo-electric pick up of the gear rotation, which are usually packed in a dry section-register. In electronic meters, a magnetic sensor monitors the liquid meter rotor revolutions and generates an electrical signal indicative of the water flow. The sensor may be based, for example, on an inductive coil, a Hall effect sensor, or a magnetoresistive device. Some devices use optical pick-up systems to read the revolution of the magnetically driven revolutions of the rotor. The consumption and/or rate data is measured at various times and the data is transmitted to a central server typically via an RF link. AMR systems can also perform mass balance calculations by registering input and output flow at different locations in a pipe network. However, the AMR systems cannot detect leaks in pipes that are below their measurement threshold. AMR systems also cannot detect leaks that are less than 1% of the nominal flow in the distribution pipes nor locate the leak as the mass balance is done over a relatively large pipe network. Recently ultrasonic flow meters have been introduced that are based on sound velocity or Doppler phase shift measurements.

Several leak detection system and methods are known, such as vibration data loggers and correlators that measure pipe vibrations that are generated by the characteristic flow turbulence caused by a leak. This leakage detection is mostly based on vibration energy measurements and locating points where the vibration energy exceeds a particular threshold. A leak detection system based on vibration sensing is disclosed, for example, in U.S. Pat. No. 7,596,458.

Vibration data loggers include a vibration sensor such as a piezo element that is attached to a pipe element. The data logger is programmed to measure vibrations at certain times mostly at night when the flow is minimal. The signal processing of the logger calculates the vibrational energy at several locations of the pipe network, stores the calculated energies in a memory, and transmits the calculated energies to a processing station for leak detection using correlation analysis. Correlation analysis requires synchronization of the clocks of the sensors, and any drift in the clocks can adversely affect the accuracy of leak location.

The accuracy of the leak detection is increased with increasing number of sensors distributed over the pipeline network. A high density of the sensors provides high resolution and improved detection probability but increases the cost of the system. Nonetheless, existing noise loggers are very sensitive to artifacts due to noise generated by water consumption flow rather than leakage.

SUMMARY OF THE INVENTION

In its first aspect, the present invention provides a system for leak detection and location in a pipe network. The system of the invention comprises two or more flow meters and a two or more vibration detectors. Each flow meter and vibration detector is provided with a microprocessor and a transceiver that allows each flow meter and vibration detector to transmit data to a service center over a communication network and, in some embodiments, also to receive data from the service center The service center processes data received from the flow meters and vibration detectors and analyzes the data for the detection of a leak in the pipe network, as explained below. When a leak is detected in the pipeline, the service center issues an alert. The alert may display on a map of the pipe network the location of any detected leaks.

In one embodiment, each of one or more of the flow meters is integrated with a vibration detector in an integrated unit.

In a second aspect, the invention provides a method for processing signals generated by the flow meters and vibration detects for detection and location of leaks in the pipe network. In accordance with this aspect of the invention, the processing uses flow data obtained from the flow meters to reduce vibration measurement artifacts. In one embodiment, vibration detection is performed essentially simultaneously with flow metering. As explained below, this allows vibrations due to an inappropriate leak to be distinguished from vibrations due to the flow of fluid that occurs during normal consumption.

In another of its aspects, the invention provides an integrated device comprising a flow meter and a vibration detector that may be used in the system of the invention. The integrated device comprises a wet chamber through which a fluid flows and is metered, and a dry chamber containing a vibration detector.

Thus, in one of its aspects, the invention provides a system for leak detection of a fluid in a pipe network comprising:
  (a) two or more flow meters adapted to be installed on a pipe at a location in the pipe network, each flow meter generating a signal indicative of a flow rate of the signal at the location of the flow meter;
  (b) two or more vibration detectors adapted to be attached to a pipe at a location in the pipe network, each vibration detector generating a signal indicative of vibrations in the pipe at the location of the vibration sensor; and
  (c) a processor configured to analyze the signals generated by one or more of the flow meters and one or more of the vibration detectors to identify the presence of one or more leaks in the pipe network.

The flow meters and vibrations detectors may communicate with the processor over a communication network, and each flow meter and each vibration detector may comprise a transceiver for communicating with the processor over the communication network. The processor may be further configured to generate an alert when a leak is detected. The system may comprise a display device, and generating an alert may comprises indicating a location of a leak in the pipeline network on a map of the network displayed on a display device. At least one flow meter may be integral with a vibration detector. The vibration detectors may be of a type selected from an accelerometer, a strain-gage or hydrophone.

In another of its aspects, the invention provides a method for detecting and localizing leaks in a pipeline network comprising:
(a) monitoring vibration signals generated by vibration detectors deployed at two or more locations in the network;
(b) determining whether there are any significant flow rates in the pipeline;
(c) if no significant flows are detected in the pipeline, executing a leak detection algorithm on the vibration signals to locate leaks in the pipeline; and
(d) issuing an alert when a leak has been located in the pipeline.

The method of the invention may comprise steps of:
(a) monitoring vibration signals generated by vibration detectors deployed at two or more locations in the network;
(b) analyzing the vibration signals to determine whether any of the vibration signals are indicative of exceptional vibrations in the network;
(c) when exceptional vibration signals are detected, monitoring signals generated by vibration detectors deployed at two or more locations in the network and flow meters deployed at two or more locations in the network;
(d) determining whether there are any significant flow rates in the pipeline;
(e) if no significant flows are detected in the pipeline, executing a leak detection algorithm on the vibration signals to locate leaks in the pipeline; and
(f) issuing an alert when a leak has been located in the pipeline.

In the method of the invention, an exceptional vibration may be a vibration whose amplitude or power exceeds a predetermined threshold, or a vibration whose amplitude or power has increased over a recent time period by a predetermined factor. The vibration signals may be monitored periodically. A trigger for monitoring the flow signals and the vibration signals may originate from a central server, from an external clock, or from a roaming vehicle. The leak detection and location algorithm may be based on the arrival times of vibrations at the vibration detectors, the pipe network configuration, and the speed of propagation of the vibrations. The leak detection and location algorithm may comprise calculation of a cross-spectrum or correlation of pairs of signals and identifying an optimal filter corresponding to maxima of coherence of the two signals.

In another of its aspects, the invention provides a device comprising a flow meter integral with a vibration detector. The flow meter may contained in a wet chamber, and the vibration detector may be coupled to the wet chamber. The vibration detector may comprise a piezo membrane placed at the bottom of the dry chamber. The device of the invention may further comprise a transceiver configured to transmit signals to a remote processor. The transceiver may also be configured to receive signals from the remote processor. The wet chamber may be separated from the dry chamber by a surface having the shape of a truncated cone and wherein a space between the wet chamber and the dry chamber contains an acoustically coupling material. The vibration detector may comprise a piezo membrane having an annular shape. The device may comprises an ultrasound transducer having a first mode in which the ultrasound transducer serves as the flow meter and a second mode of operation in which the ultrasound transducer servers as the vibration detector. The ultrasound transducer in the first mode of operation may measure transmitted ultrasound waves for phase shift or frequency shift. The ultrasound transducer in the second mode of operation may measure low frequencies related to acoustic waves generated in a water network. The device may be configured to detect malfunctions in the device.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 6a shows a vibration signal detected by an independent vibration detector mounted on a metal pipe, FIG. 6b shows a vibration signal measured simultaneously on the same metal pipe by a vibration detector in an integral device comprising the vibration detector and a flow meter; and FIG. 6c shows the Fourier transform of the signals of FIGS. 6a and 6b; and FIG. 7a shows a vibration signal detected by an independent vibration detector mounted on a metal pipe, FIG. 7b shows a vibration signal measured simultaneously on the same metal pipe by a vibration detector in an integral device comprising the vibration detector and a flow meter; and FIG. 7c shows the Fourier transform of the signals of FIGS. 7a and 7b.

DETAILED DESCRIPTION OF EMBODIMENTS

Figure 1A:
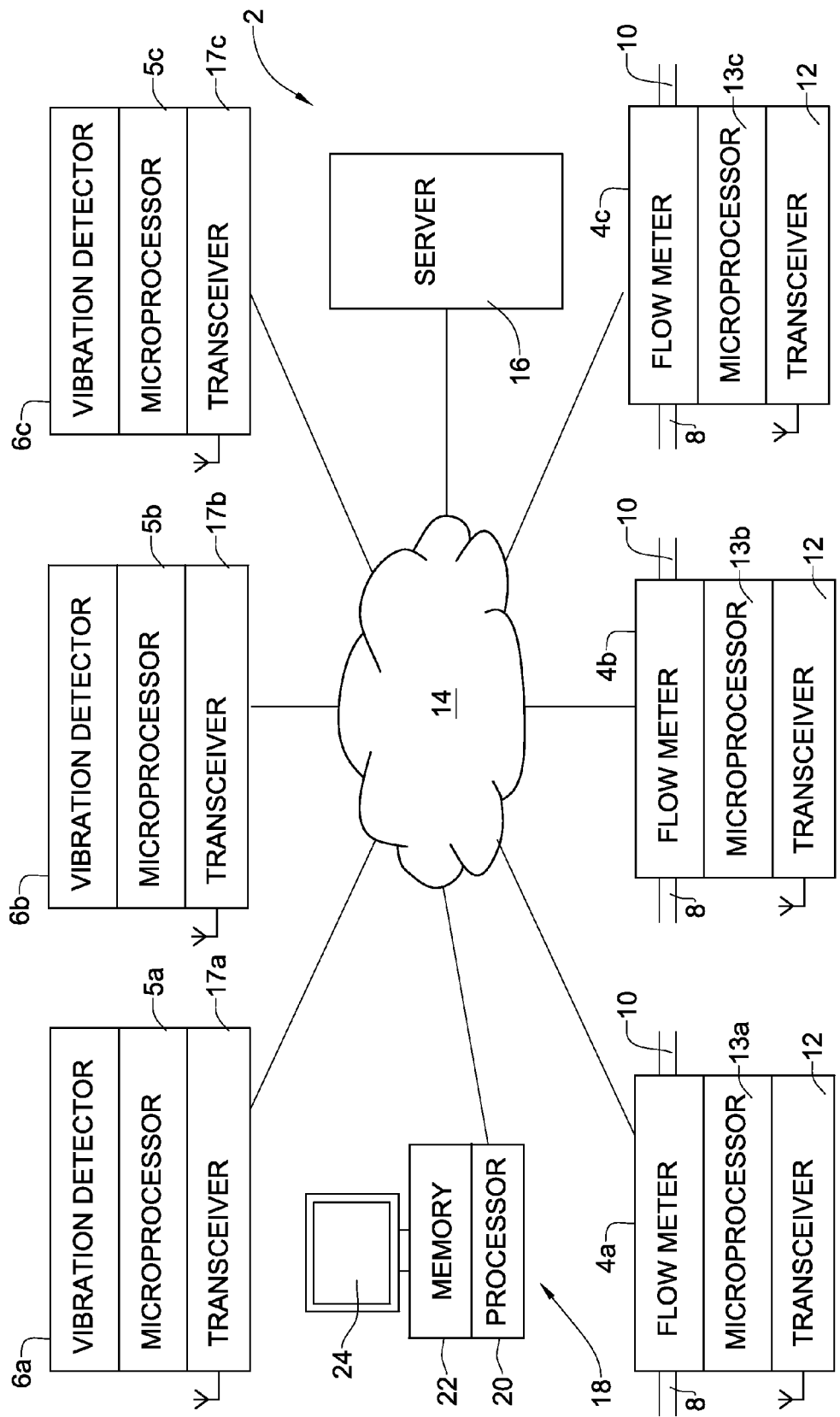
FIG. 1a shows a system for leak detection and location in a pipeline network in accordance with one embodiment of the invention having separate flow meters and vibration detectors.

FIG. 1a shows a system 2 for leak detection in a pipe network, in accordance with one embodiment of this aspect of the invention. The system 2 comprises two or more flow meters 4 and a plurality of vibration detectors 6. Three flow meters 4a, 4b, and 4c, and three vibration detectors 6a, 6b, and 6c, are shown in FIG. 1. This is by way of example only, and the system of the invention may be implemented using any number of flow meters that is at least two, and any number of vibration detectors that is at least two. The number of flow meters may be less than, equal to or greater than the number of vibration detectors. The flow meters may be any flow meter known in the art. Each flow meter has a flow inlet 8 and a flow outlet 10 that allows the flow meter to be installed on a flow line at a location in the pipe network. The vibration meters 6 may be any type of vibration detector known in the art, such as an accelerometer, strain-gage or hydrophone type sensor. The hydrophone tends to be more suitable for plastic pipes providing better performance than the accelerometer. Each vibration meter 6 is adapted to be attached to a pipe in the pipe network. The typical vibration frequencies are in the range of 1-100 Hz for plastic pipes and 500-2000 Hz for metal pipes.

Each flow meter 4 is provided with microprocessor 13 and a transceiver 12 that allows each flow meter to transmit data to a server 16 over a communication network indicated by the cloud 14 and further allows the flow meter to receive data from the server 16. Similarly, each vibration detector 6 is provided with a microprocessor 5 and a transceiver 17 that allows the vibration detector to communicate with the server 16 over the communication network 14.

The vibration detector may be attached to a pipe in the pipe network adjacent to a flow meter.

The system 2 further includes a service center 18 that that communicates over the communication network 14 with the server 16, and through the server 16, with the flow meters 4 and the vibration detectors 6. The service center 18 includes a processor 20 that processes data received from the flow meters and vibration detectors and analyzes the data for the detection of a leak in the pipe network, as explained below. Data received at the service center, as well as the results of any processing or analysis of the data may be stored in a memory 22. When a leak is detected in the pipeline, the processor 20 issues an alert. The alert may be displayed on a display device, such as a CRT screen 24. The alert may include the location in the pipe network of any detected leaks.

Figure 1B:
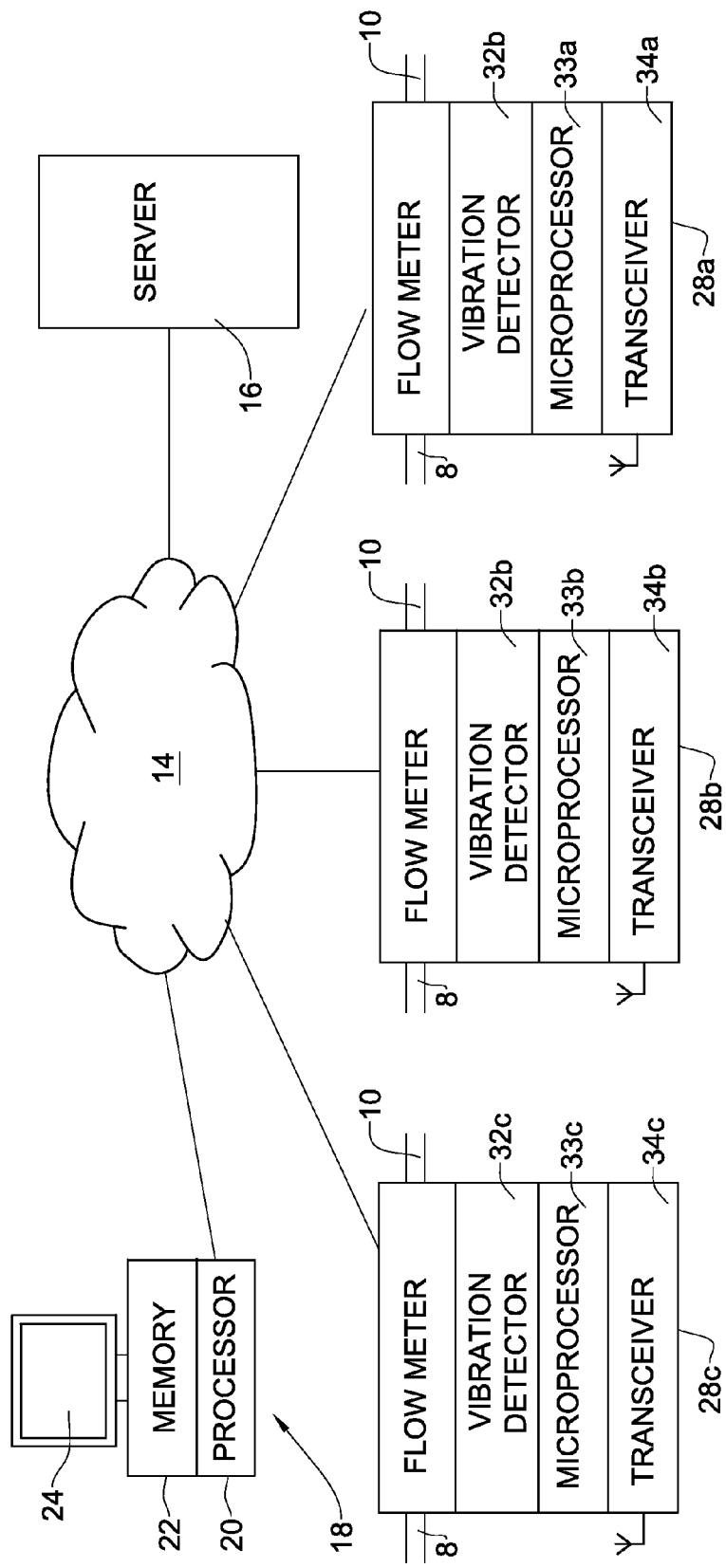
FIG. 1b shows a system for leak detection and location in a pipeline network in accordance with a second embodiment of the invention having integrated flow meters and vibration detector.

FIG. 1b shows a system 2' for leak detection in a pipe network, in accordance with another embodiment of this aspect of the invention. The system 2' has several elements in common with the system 2 of FIG. 1a, and similar components are indicated by the same reference numeral in FIGS. 1a and 1b, without further comment. The system 2' comprises a plurality of devices 28 comprising a flow meter 30 integral with a vibration detector 32 that may be assembled in a common housing. In an alternative design, the flow meter 30 and the vibration detector 32 of the device 28 are in separate housings but share a common microprocessor 13. Three devices 28a, 2bb, and 28c, are shown in FIG. 1b. This is by way of example only, and the system 2' may include any number of integrated units 28 that is at least two. Each device 28 also includes a transceiver 34 that communicates with the server 16 over the communication network 14. In this embodiment, the flow meter 30 measures the flow at the same location in the pipe network where the associated vibration detector detects vibrations.

In one embodiment, the communication network 14 is a wireless network, for example, using any known RF protocol, such as Hubs or Cellular, Ethernet or TCP-IP. The communication can be one way from each vibration detector 6, flow meter 10 or integrated device 10 to the server 16. Alternatively, the communication between each vibration detector 6, flow meter 10 or integrated device 10 to the server 16 is two-way. For example, the server 16 may transmit data to the sensors in order synchronize the clocks of the vibration detectors or flow meters, or may send commands or set parameter values of the meters and detectors.

The vibration detector 6 or 32 when attached to a pipe in the pipe network, detects pipe vibrations or acoustic waves in the fluid generated by a leak and arriving through the network to the detector. The vibration sensor signal is amplified, converted to a digital signal, for example, at a sampling rate of 5 kHz and a dynamic range of 12 bit. Typical vibrations at frequencies above 500 hz in metal water pipes range from between $10^{-4}$-$10^{-3}$ m/sec$^2$ in the absence of a leak to about $10^{-3}$-$10^{-2}$ m/sec$^2$ in the presence of a leak. The typical frequencies generated by small leaks are about 1-8 kHz, but the high frequencies undergo larger attenuation than low frequencies thus a sampling rate of 5 kHz with a low pass filter of 2 kHz can provide an adequate signal for leak detection. For plastic water pipes the frequencies are lower, in the range of 10-200 Hz, and the vibrations have a lower amplitude. Therefore for a plastic pipe, the sampling rate should be around 600 samples per second and a low pass filter. When some of the pipes are made of plastics such as PVC or PU, the server can configure the sensor modules to measure vibration at a higher sensitivity and in a lower frequency band.

The microprocessor associated with the flow meters and vibration detectors may be, for example, a CC430 microprocessor from Texas Instruments having integrated ADC and RF circuits. The microprocessor may have an internal clock in which case the microprocessor may be configured to activate the flow meters and vibration detectors at predetermined times. The signals of the vibration detectors and the flow meters are input to the microprocessor. In the case of the integrated device 28, the vibration detector signal and the flow meter signal may be input into the processor 33 via separate digital channels or via multiplexer (not shown). The microprocessor digitizes the signals. The microprocessor may transmit the raw data signals to the service center for processing. The microprocessor may preprocess the signals, and transmit the results of the preprocessing to the service center. The preprocessing may include filtering noise from the signal. The processing may include calculating a flow rate from the signals generated by the flow meters. The processing may include calculating a Fourier transform of the signals generated by the vibration detectors and performing a peak search or power estimation in the Fourier transform. Processing of the vibration signals may use AR or LPC modeling of the signal spectra that is phase preserving. Signal modeling in a particular frequency band can be effective since pipes have characteristic frequency bands in which they transmit vibrations effectively. The frequency band can be predetermined when the system is calibrated or by raw signal analysis at the server by coherence analyses. In another embodiment, the vibration power or amplitude in pipes due to the leak is determined is by the microprocessor and the determined power or amplitude is transmitted to the server. The power estimation is done by filtering the vibration signal using analog circuits or a microprocessor and calculating the average power of the signal in a predetermined time window, typically of about 0.5 sec. The estimated power is a number that can be easily stored and transmitted to the server with low battery power consumption.

The data may be transmitted from the device to the service center 18 on the fly, or alternatively, the microprocessor may store data in a memory (not shown), and transmit the data to the service center 18 at predetermined times. Each flow meter 4 and each vibration detector 6 in the system 2, or each integrated device 28 in the system 2' has an ID number that is transmitted to the service center with the data.

Figure 2:
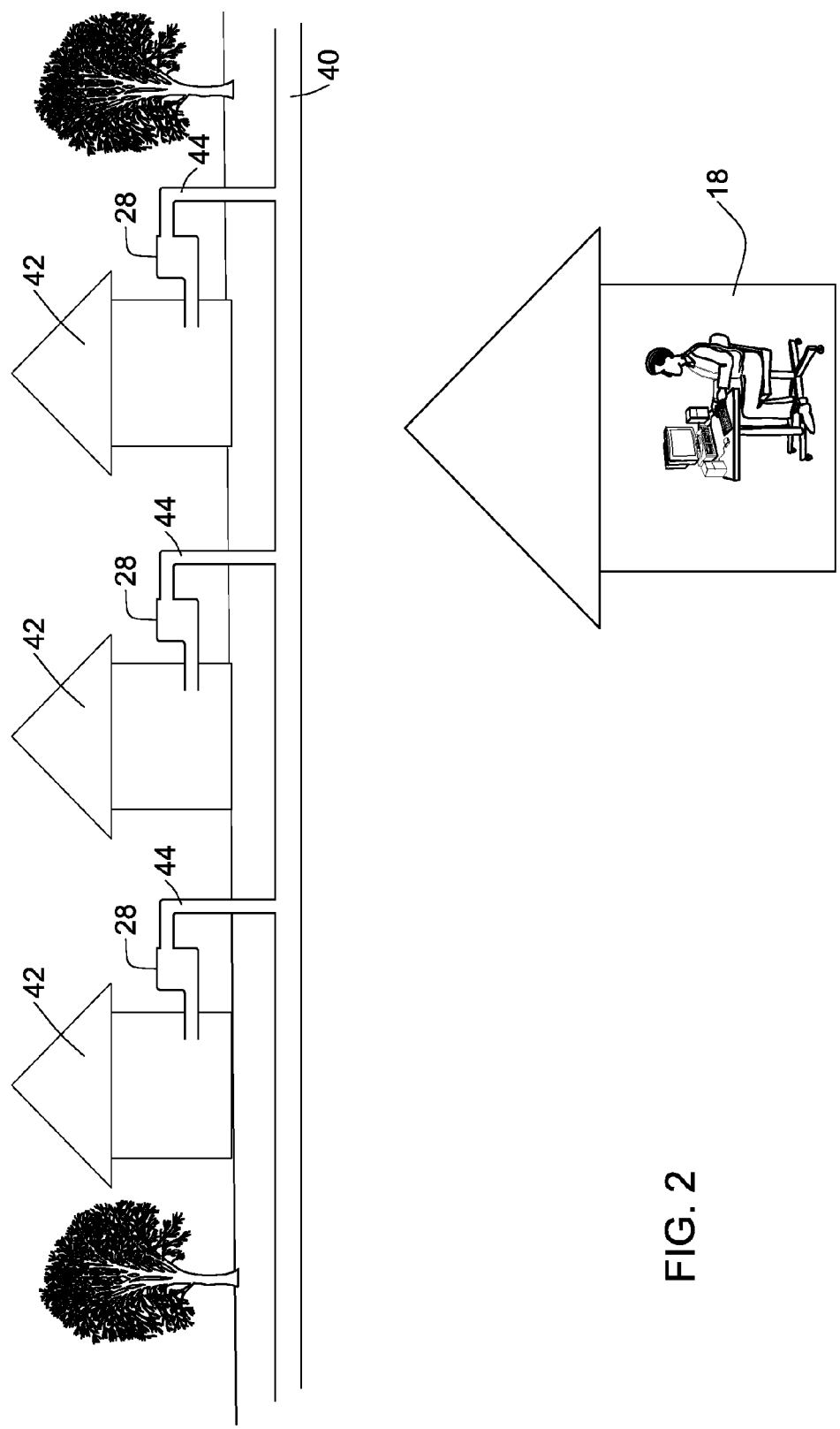
FIG. 2 shows the system of FIG. 1b deployed on a pipeline network.

FIG. 2 shows the system 2' of FIG. 1b deployed on a pipe network. An underground pipe 40 that is part of the pipe network conducts a fluid such as water or gas from a source (not shown in FIG. 2) to each of a plurality of buildings 42. Each of the buildings 42 is provided with an individual feeder line 44 that conducts the fluid from the underground pipe 40 to the building. On each feeder line 44 a device 28 is deployed. The feeder line 44 is connected to the input port 10 of the flow meter 30 of the device 28. Fluid exits the device 28 at the output port 8 of the flow meter 30 of the device 28 at the in port 10 of the device 28 and then enters the building. Each deployed device 28 measures flow of the fluid through the device 28, and also detects vibrations in the feeder pipe 44 to which the device 28 is attached. Data collected by each device 28 are transmitted to the service center 18, as explained above.

Activation of the flow meters and vibration detectors and transmission of data between the devices and the service at predetermined times allows a significant reduction in the power requirements of the system. The system can be maintained be in a stand-by (sleep) mode and woken up on schedule to perform tasks and then returned to the sleep mode until the next scheduled activation. When a leak occurs in the pipe network, vibrations are generated in the fluid emanating from the leak location. Vibration detection is typically performed only a few times a day or week, preferably at night when the flow is minimal. In one embodiment, vibration detection is performed when the flow rate is minimal. The vibration recording can be 0.5-1 second for estimation of vibration power, while a longer recording time in the order of 2-10 seconds might be preferred for correlating the signals for leak location.

The service center 18 receives the signals from all of the flow meters and vibration detectors in the system. The processor 20 of the service center executes an artifact detection and rejection algorithm based on flow estimation in proximity to the locations where vibrations were detected. The vibration power detected by each vibration detector in the system, or the power in a predetermined frequency band, may be indicated on a map of the pipe network and displayed on the display. The frequency band may be selected according to the material of the pipes in the pipeline. The vibration power may be indicated as color code to draw a user's attention to vibration detectors reporting unusually high. Trends in the vibration power and the flow rates can also be displayed. If the value at a particular sensor exceeds the threshold or significantly increases relative to a previous value recorded by the detector, this could be indicated on the display. Trends in the vibration power and the flow rates at specific places with increased vibration power can be presented to the operator.

In addition, the processor 20 of the service center processes the received signals for the detection and location of leaks in the pipe network. In accordance with the invention, the processing uses flow data obtained from the flow meters to reduce vibration measurement artifacts. This allows vibrations due to an inappropriate leak to be distinguished from vibrations due to the flow of fluid that occurs during normal consumption.

Figure 3A:
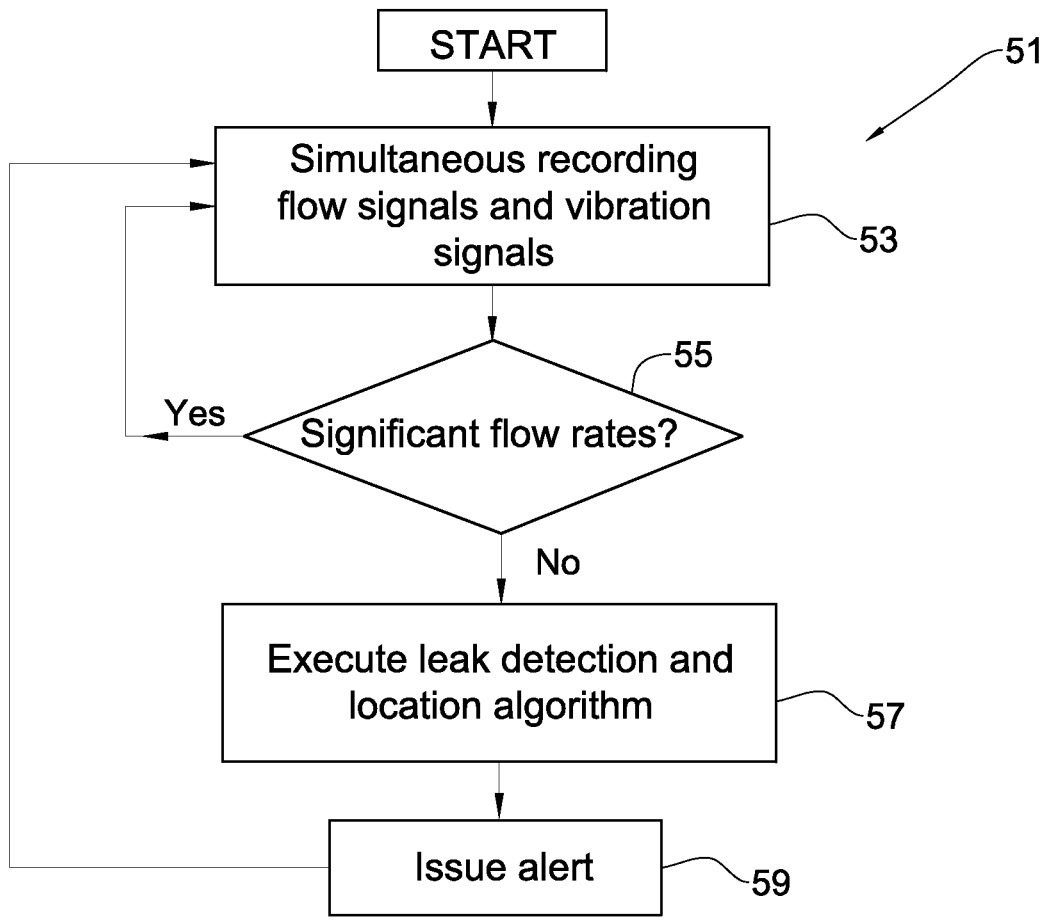
FIG. 3a shows a flow chart for a method of leak detection and location in accordance with one embodiment of the invention.

FIG. 3a shows a flow chart for a process 51 for detecting and localizing leaks in a pipeline network in accordance with one embodiment of the invention. In step 53 simultaneous recording of flow signals and vibration signals is carried out. The trigger for recording the signals may originate from the server which activates the flow meters and vibration detectors at predetermined times, under predetermined circumstances. Alternatively, a vibration detector detecting an exceptional vibration may issue a trigger for simultaneous recording of the flow signals and the vibrations signals. As yet another alternative, the flow meters and vibration detectors may receive a signal from a common clock, such as from a geopositioning system (GPS) or a cellular network, and simultaneous recording of the flow signals and the vibration signals occurs at predetermined times. In another embodiment, a roaming vehicle generates a series of synchronization signals and collects the recorded signals and transmits the signals to the server. In step 55, it is determined whether there are any significant flow rates that may introduce an artifact into the leak detection. A significant flow rate may be, for example, consumption by a user above certain value that can introduce significant vibration into the network similar to the vibration caused by a leak. If yes, the process returns to step 53 with the recording of the flow and vibration signals. If no, the process proceeds to step 57 where a leak detection and location algorithm is executed on the recorded signals. If a leak is detected and located, then in step 59 an alert is issued and the process returns to step 53.

Figure 3B:
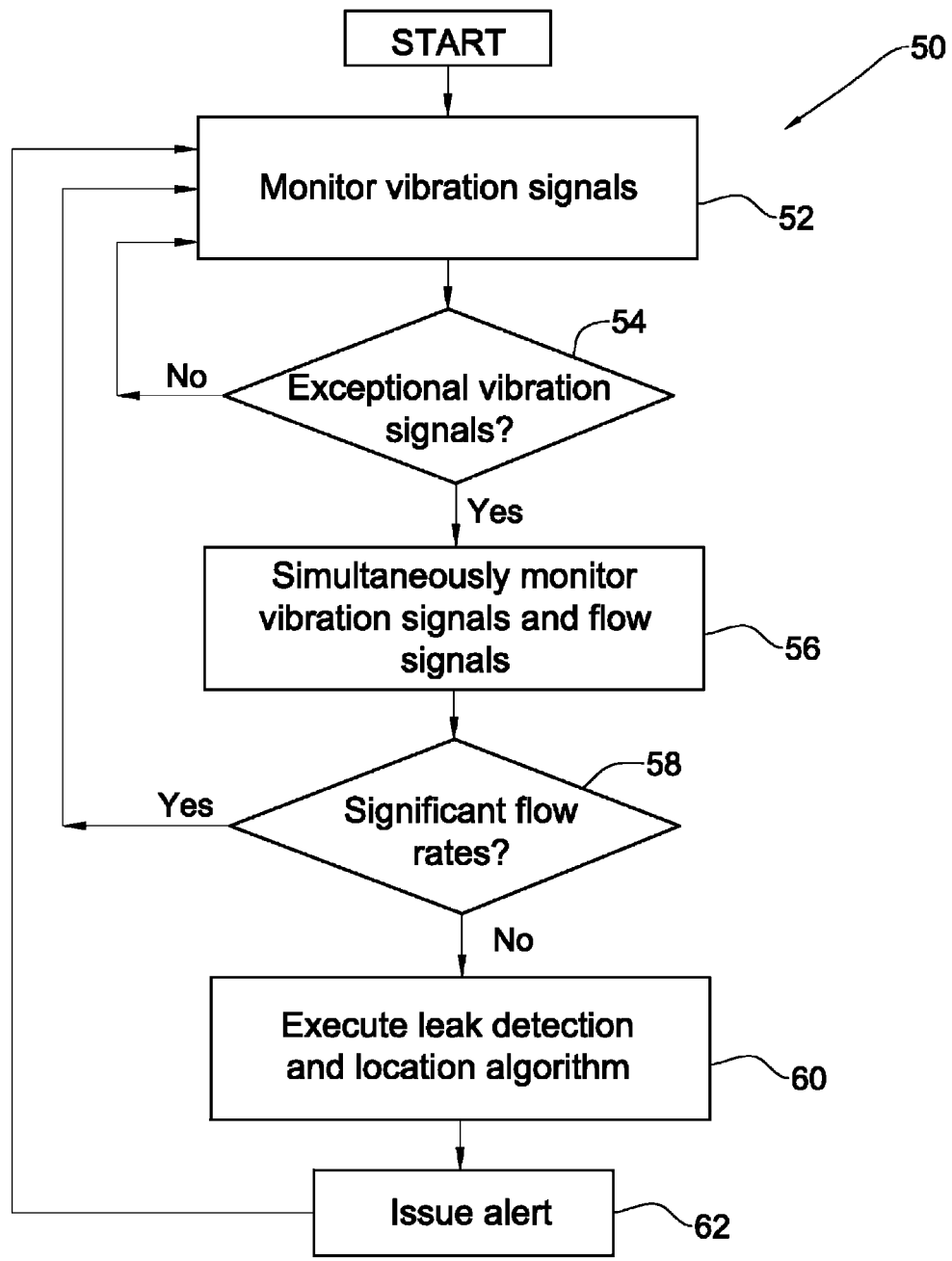
FIG. 3b shows a flow chart for a method of leak detection and location in accordance with a second embodiment of the invention

FIG. 3b shows a flow chart for a process 50 for detecting and localizing leaks in a pipeline network in accordance with another embodiment of this aspect of the invention. The process 50 begins with the monitoring of vibration signals generated by vibration detectors deployed at various locations in the network. Monitoring of the vibration signals may be periodic, for example, at one or more predetermined times over a 24 hour period. In step 54, when vibrations signals have been obtained, the signals are analyzed to determine whether any of the vibration signals indicated exceptional vibrations in the network. An exceptional vibration may be, for example, a vibration whose amplitude or power exceeds a predetermined threshold, or a vibration whose amplitude or power has increased over a recent time period by a predetermined factor. If no exception vibration signals are detected, the process returns to step 52 and the monitoring of the vibration signals continues. If in step 54 it is determined that exceptional vibration signals have been detected, then the process continues with 56 where vibration signals from at least some of the vibration detectors and some of the flow rate signals from the flow detectors are monitored synchronously. The inaccuracy of the timing of the synchronous recording of the vibration is preferable be less than 1 ms, as a delay of every 1 ms in the timing of the readings can introduce an error in the leak location of about 1.2 meters. The process then continues with step 58 where it is determined whether there are any significant flow rates in the pipeline. The flow rate estimation is based on the reading of the water flow meters in the area where the vibration is detected. If yes, then there is a great chance for a false positive (a flow due to consumption being interpreted as a leak) so that reliable leak detection or location is not possible, and the process returns to step 52 with the continuation of the monitoring and recording of the vibration signals. If at step 58 it is determined that there is no significant flow in the pipeline, the process continues to step 60 where a leak detection and location algorithm is executed which analyzes the vibration signals in order to locate leaks in the pipeline. After leak detection and location, an alert is issued (step 62). The alert may an audible or visual signal. The alert may involve indicating the location of the leak on a map of the pipeline displayed on the display 24, whereupon the process returns to step 52 and the monitoring of the vibration signals continues.

The leak detection and location algorithm executed in step 60 of the process 50 is based on the arrival times of vibrations at the various vibration detectors, together with the pipe network configuration, and the speed of propagation of the vibrations. Vibrations arrive at each vibration detector with a time lag proportional to the distance of the detector from the leak (the origin of the vibrations). The velocity of vibrations in pipes is around 1250 m/s. A precision of around 2 meters in the location of the leak is usually satisfactory.

The leak detection and location algorithm may involve, for example, calculation of the cross-spectrum (coherence) of pairs of signals and identifying the optimal filter that corresponds to the maxima of the coherence of the two signals. Alternatively, pairs of signals may be filtered in a maximal coherence spectral band, and calculating the cross correlation of the filtered signals. Another method uses finding the correlation maxima. When the correlation exceeds a predetermined threshold, the leak position can be determined from the time of the correlation or cross-cepstrum maxima times the sound velocity in the pipes.

In another embodiment, the leakage detection and location is based on flow metering and vibration power in a particular frequency band that is measured by each vibration sensor, either synchronously or not synchronously. The advantage of this method is the ability to transmit a small data volume over one way communication link. The power estimation is done at certain times at night, by recording and filtering the vibration signal using analog circuits or microprocessor and calculating the average power of the signal in a predetermined time window, typically of about 0.5 sec. The measured vibration power and the flow value is sent to the server over the communication network with a sensor identifier (ID) and time stamp. Each sensor is associated with the geographical position according to its installation. The first step is artifact rejection using flow meter data. For each vibration measurement the flow rate in the radius of 100-200 meters is estimated based on the flow meter data. If the flow is larger than a defined threshold the vibration data for the specific measurement is labeled as unreliable. The flow threshold is calculated for each area based on the statistics of the night flow. Reliable vibration measurements are added to the list of measurements that is currently updated. The second step is calculating the average (or 5-30 quantile) vibration power of the reliable measurements for every sensor in a time window of 1-5 days in order to reduce measurement noise. The leak detection is performed by finding a maximum of the averaged vibration power that is above certain threshold. The threshold can be a predetermined value or calculated adaptively for each area and time of the year using statistics e.g. three times the standard deviation of the vibration power of the sensors in an area of about 50 sensors. The maximum value and position can be optimized using fitting of the two-dimensional function of vibration power $P(x,y)$, where x-y are geographical coordinates. The fitting can be performed by a spline function. Another method for location of the leak more precisely between the vibration sensors is solving an inverse problem of finding a vibration source using the data of vibration sensors at specific points. This method uses the pipe geometry and attenuation coefficients of the acoustic waves in the specific pipes as well as reflection coefficients in the pipe joints.

Figure 4:
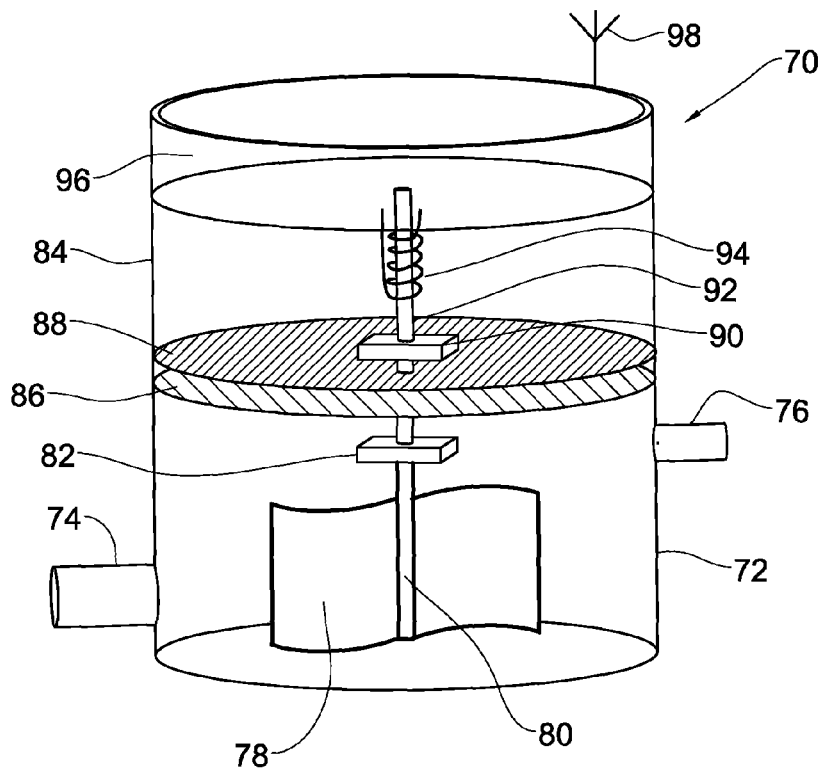
FIG. 4 shows an integrated flow meter and vibration detector in accordance with one embodiment of the invention.

FIG. 4 shows an integrated device 70 comprising a flow meter and a vibration detector that may be used for the device 28 in the system 2' shown in FIG. 1b, in accordance with one embodiment of this aspect of the invention. The integrated device 70 comprises a wet chamber 72 through which a fluid flows between an inlet port 74 and an outlet port 76. Flow of a fluid through the wet chamber causes a vane 78 to rotate about an axis 80. Rotation of the axis 80 drives rotation of a magnet 82, so that rotation of the vane 78 is coupled to rotation of the magnet 82. The integrated device 70 further comprises a dry chamber 84. The dry chamber 84 is separated from the wet chamber by a space filled with an acoustically coupling layer 86 that conducts vibrations from the wet chamber 82 to a piezo membrane 88 placed at the bottom of the dry chamber 84. The acoustically coupling material may be, for example, silicone rubber. The acoustic coupling material may be compressible to allow easy attachment of the dry chamber to the wet chamber A magnet 90 located in the dry chamber rotates about an axis 92 when driven by the rotation of the magnet 82 in the wet chamber 72. Thus, rotation of the vane 78 is coupled to rotation of the magnet 92. Rotation of the magnet 90 generates a signal that can be calibrated with the flow rate in the wet chamber 72. The signal may be an electrical signal generated in a wire coil 94 or an optical signal (not shown). The piezo membrane 88 generates an electric signal that can be calibrated with vibrations in the membrane 88, and may be, for example, a polarized PVDF film or piezo ceramic material such PZT. An amplification and processing unit 96 receives the signals generated by the magnet 92 and the piezo membrane 88. The processing unit 96 includes a microprocessor and a transceiver (not shown) and an antenna 98, as explained above with reference to the device 28 shown in FIG. 1b.

Figure 5:
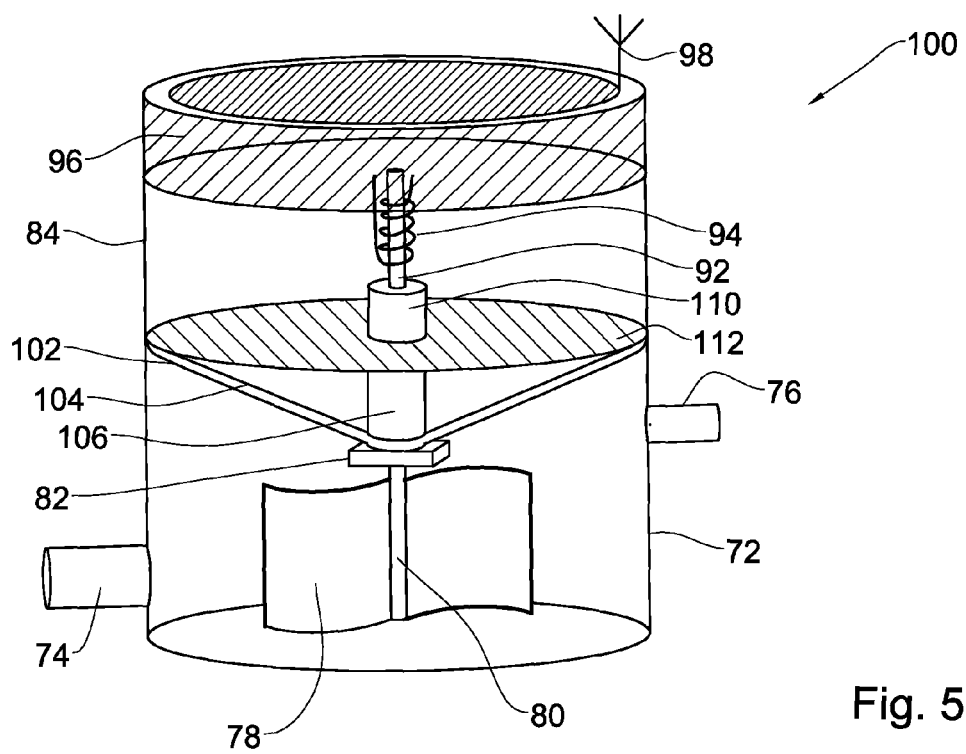
FIG. 5 shows an integrated flow meter and vibration detector in accordance with another embodiment of the invention.

FIG. 5 shows an integrated device 100 comprising a flow meter and a vibration detector that may be used for the device 28 in the system 2' shown in FIG. 1b, in accordance with another embodiment of this aspect of the invention. The integrated device 100 has several components in common with the integrated device 70 shown in FIG. 4, and similar components are indicated by the same reference numerals without further comment. In the device 100, the interface between the wet chamber 72 and the dry chamber 84 has the shape of an inverted truncated cone. A space 102 in the interface contains an acoustically coupling material 104. An opening in the truncated conical surface of the dry chamber is covered with a flexible membrane 108. A magnet 110 extends from the flexible membrane 108 into the dry chamber 84. Rotation of the magnet 110 is coupled to the rotation of the magnet 82 as explained above with reference to the magnet 90 of the integrated device 70 shown in FIG. 4. Rotation of the magnet 110 thus generates a signal that can be calibrated with the flow rate of fluid in the wet chamber 72. The magnet 110 is surrounded by a cylindrical coupler 106 that conducts vibrations from the acoustically coupling material 104 to a piezo membrane 112. The piezo membrane 112 generates a signal that can be calibrated with vibrations in the membrane 112. The membrane 112 has an annular shape and surrounds the magnet 110. In another embodiment, the truncated conical surface of the dry chamber is corrugated to conduct vibrations from the acoustically coupling material to the peizo membrane instead of, or in addition to, the cylinder 106.

In other embodiments, flow detection utilizes an optic sensor that measures rotor revolutions, or ultrasound sensors that are used to measure transit time or Doppler shift that can be calibrated with flow rate.

In some embodiments of the integrated device, flow rate metering and vibration detection is performed using a common ultrasound transducer. The ultrasound transducer has a flow metering mode of operation in which the ultrasound transducer measures transmitted ultrasound waves for phase shift or frequency shift that is caused by liquid or gas flow and generates a signal that can be calibrated with the flow rate. In this mode, only transmitted frequencies are used and all the other frequencies are filtered out. The ultrasound transducer also has a vibration detection mode in which the ultrasound transducer measures low frequencies and generates a signal that can be calibrated with the vibrations.

The processor may also be configured to analyze the flow meter signals and vibration detection signals to detect a malfunctioning flow meter. This can be done, for example, by trend analysis of the vibrations and flow reading, for example, by comparing the vibration signal power in one or several frequency bands, to the flow rates. For example, if the rotor of a flow meter is stuck or is slowed by an external magnet, the flow becomes more turbulent and creates more vibrations than during normal operation. By detecting the increased vibrations of a flow meter at different flow rates, the server can issue an alarm for malfunction of the flow meter.

Experiments were carried out to compare vibration detection by an integrated device of the invention comprising a flow meter and a vibration detector with vibration detection by a vibration detector independent of a flow meter. The integrated device of the invention was constructed by fitting a piezo membrane to a flat register in a bronze Badger™ water meter. A Wilcoxon™ accelerometer 728a (sensitivity 500 mv/g) was used as the independent vibration detector. Both the integrated device and the independent vibration detector were mounted on a pipe. Vibrations in the pipe were induced by opening a tap. FIG. 6a shows the vibration detected by the independent vibration detector, and FIG. 6b shows the vibrations detected simultaneously by the integrated device when mounted on a metal pipe. FIG. 6c shows the Fourier transform of the signal in FIG. 6a (120) and the signal shown in FIG. 6b (122). FIG. 7 shows results of vibration detection by the same detectors when mounted on a plastic pipe. FIG. 7a shows the vibration detected by the independent vibration detector, and FIG. 7b shows the vibrations detected simultaneously by the integrated device when mounted on a metal pipe. FIG. 7c shows the Fourier transform of the signal in FIG. 7a (124) and the signal shown in FIG. 7b (126). The results show that the integrated device has a greater sensitivity, particularly at low frequencies, which includes the frequencies of interest in leak detection.

The invention claimed is:

1. A system for leak detection of a fluid in a pipeline network, comprising:
    a plurality of flow meters integrated with vibration sensors deployed at two or more locations in the pipeline network, each said flow meter integrated with said vibration sensor comprising:
        a wet chamber comprising the flow meter, the flow meter configured to generate a flow signal indicative of the fluid flow through the wet chamber;
        a dry chamber comprising a piezo membrane as a vibration sensor placed at the bottom of the dry chamber, wherein the piezo membrane is configured to generate a vibration signal, that is calibrated with vibrations in the piezo membrane, caused by the fluid flow;
        an interface separating the wet chamber from the dry chamber comprising an acoustically coupling material configured to conduct vibrations from the wet chamber, caused by a leak in the pipeline network and introduced by the fluid flow through the wet chamber, to the dry chamber and to the piezo membrane of the dry chamber; wherein the acoustically coupling material is compressible to allow attachment of the dry chamber to the wet chamber;
        a processor configured to receive and process the signals generated by the flow meter and the piezo membrane; and
        a transceiver configured to transmit and receive the signals to at least one remote processing unit; and
    the at least one remote processing unit configured to receive the flow signals and the vibration signals from each of the plurality of flow meters integrated with the vibration sensors, and perform an artifact detection and rejection algorithm for reducing vibration measurement artifacts due to noise generated by water consumption flow rather than leakage to detect and localize leaks in the pipeline network based on said flow signals and said vibration signals during leak detection.

2. The system for leak detection according to claim 1, wherein the interface separating the wet chamber from the dry chamber comprising a shape of a truncated cone and wherein a space between the wet chamber and the dry chamber contains the acoustically coupling material.

3. The system for leak detection according to claim 1, wherein the flow meter of the plurality of flow meters integrated with the vibration sensors are at least one of a vane and an ultrasound transducer.

4. The system for leak detection according to claim 1, wherein the piezo membrane has an annular shape and surrounds a magnetic drive.

5. The system for leak detection according to claim 1, wherein the processor of the flow meter integrated with vibration sensor is configured to detect malfunction in the flow meter integrated with the vibration sensor based on a flow rate of the flow meter and vibrations generated in the piezo membrane.

6. A method of detecting leaks using the system for detecting leaks according to claim 1, the method comprising:
    substantially simultaneously generating the vibration signals and the flow signals by the flow meters integrated with the vibrations sensors;
    transmitting the vibration signals and the flow signals from each of the transceivers of the flow meters integrated with the vibration sensors to the at least one remote processing unit;
    monitoring the vibration signals generated by the flow meters integrated with the vibration sensors, using the at least one remote processing unit;
    analyzing the vibration signals to determine whether any of the vibration signals are indicative of exceptional vibration signals in the pipeline network; and
    when the exceptional vibration signals are detected,
    simultaneously monitoring the vibration signals and the flow signals generated by the flow meters integrated with the vibration sensors; and
    determining whether there are any significant flow rates based on the flow signals in the pipeline network in a location where the exceptional vibration signals are detected to introduce the artifact detection and rejection algorithm for reducing vibration measurement artifacts due to noise generated by water consumption flow rather than leakage, into a leak detection and location algorithm using the flow signals generated by the flow meter integrated with the vibration sensor; and
    if no significant flows are detected in the pipeline, executing the leak detection and location algorithm based on the vibration signals to locate leaks in the pipeline; and
    issuing an alert after a leak has been located in the pipeline.

7. The method according to claim 6, wherein the exceptional vibration is a vibration whose amplitude or power exceeds a predetermined threshold, or the vibration whose amplitude or power has increased over a recent time period by a predetermined factor.

8. The method according to claim 6, wherein the vibration signals are monitored periodically.

9. The method according to claim 6, wherein the leak detection and location algorithm comprises calculation of a cross-spectrum or correlation of pairs of signals and identifying an optimal filter corresponding to maxima of coherence of the two signals.

* * * * *